US00PP26313P2

(12) United States Plant Patent
Lyrene et al.

(10) Patent No.: US PP26,313 P2
(45) Date of Patent: Jan. 19, 2016

(54) BLUEBERRY PLANT NAMED 'FL07-399'

(50) Latin Name: ***Vaccinium corymbosum* L.**
Varietal Denomination: FL07-399

(71) Applicant: Florida Foundation Seed Producers, Inc., Marianna, FL (US)

(72) Inventors: Paul M. Lyrene, Micanopy, FL (US); James W. Olmstead, Gainesville, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 14/544,783

(22) Filed: Feb. 12, 2015

(51) Int. Cl.
*A01H 5/08* (2006.01)

(52) U.S. Cl.
USPC ..... Plt./157

(58) Field of Classification Search
USPC ..... Plt./157
See application file for complete search history.

(56) References Cited

U.S. PATENT DOCUMENTS

PP12,165 P2 10/2001 Lyrene
PP19,233 P2 9/2008 Lyrene

*Primary Examiner* — Anne Grunberg
(74) *Attorney, Agent, or Firm* — Dentons US LLP

(57) ABSTRACT

'FL07-399' is a new and distinct southern highbush blueberry (*Vaccinium corymbosum* L.) variety distinguished by a very low chilling requirement, high evergreen leaf retention, upright-spreading growth habit, and fruit that are large, sweet, and firm, with a small, dry picking scar.

6 Drawing Sheets

Latin name of the genus and species of the plant claimed: *Vaccinium corymbosum* L.

Variety denomination: 'FL07-399'.

BACKGROUND OF THE INVENTION

The present invention relates to a new and distinct hybrid variety of southern highbush blueberry (*Vaccinium corymbosum* L.) named 'FL07-399'. 'FL07-399' is a blueberry clone distinguished by its low chilling requirement, vigorous, upright spreading bush, and large, firm berries that ripen from mid-March through late-April when grown in South Central Florida under evergreen conditions. Several thousand plants of 'FL07-399' have been propagated by softwood stem cuttings in Gainesville, Fla., and the resulting plants have all been phenotypically indistinguishable from the original plant. Contrast is made to 'Emerald' (U.S. Plant Pat. No. 12,165), an important variety widely planted in the southeastern United States. The claimed plant is important because it is more vigorous, and has a higher tendency towards evergreeness than 'Emerald'. Fruit of 'FL07-399' are earlier maturing than that of 'Emerald'. 'FL07-399' has higher total yield than 'Emerald' when grown as an evergreen plant.

'FL07-399' originated as a seedling from a cross between 'FL03-79' (unpatented) as the female (seed) parent and 'Scintilla' (U.S. Plant Pat. No. 19,233) as the male (pollen) parent. This cross was made as part of a breeding program in a greenhouse in Gainesville, Fla., in February 2003. The seedling was planted in a high-density field nursery located in Citra, Fla., in May 2004, and the first fruit were evaluated in April 2005. After the third year of fruiting in the field, in the spring of 2007, 'FL07-399' was asexually propagated by softwood stem cuttings, and an experimental 15-plant test plot was established as part of a variety test in Windsor, Fla., in January 2008. Based on the growth, yield, and fruit quality of this plot, 'FL07-399' was repropagated by softwood stem cuttings and experimental test plots ranging from 5 to 50 plants were established near Arcadia, Citra, Interlachen, Haines City, and Waldo, Fla. These plots have been observed during flowering and ripening each year, and no mutations or off-type plants have been observed.

'FL07-399' differs from the proprietary parent 'FL03-79' (unpatented) in that 'FL07-399' is more vigorous and has larger berries. 'FL07-399' differs from the parent 'Scintilla' (U.S. Plant Pat. No. 19,233) in that 'FL07-399' is later blooming and has higher tendency towards evergreeness. 'FL07-399' differs from the commercial variety 'Emerald' (U.S. Plant Pat. No. 12,165), an important variety widely planted in the southeastern United States, in that 'FL07-399' blooms later and has a lower chilling requirement that allows it to be grown as an evergreen plant in regions conducive to this management system. 'FL07-399' berries ripen earlier and are sweeter than 'Emerald' berries.

SUMMARY OF THE INVENTION

Blueberry variety 'FL07-399' exhibits outstanding and distinguishing characteristics when grown under normal horticultural practices in Florida, including:

(1) a low chilling requirement, particularly for the flower buds;
(2) a vigorous, upright spreading bush;
(3) early ripening (50% ripe berries in North Florida around April 25, and March 15 in South Central Florida); and
(4) large, sweet berries with a small, dry picking scar.

BRIEF DESCRIPTION OF THE DRAWINGS

The accompanying photographs show typical bush, flower, and fruit characteristics for 'FL07-399'. Colors shown are as true as can be reasonably reproduced by photographic procedures and may differ from those cited in the detailed description, which accurately describes the colors of 'FL07-399'.

DETAILED BOTANICAL DESCRIPTION

Figure 1:
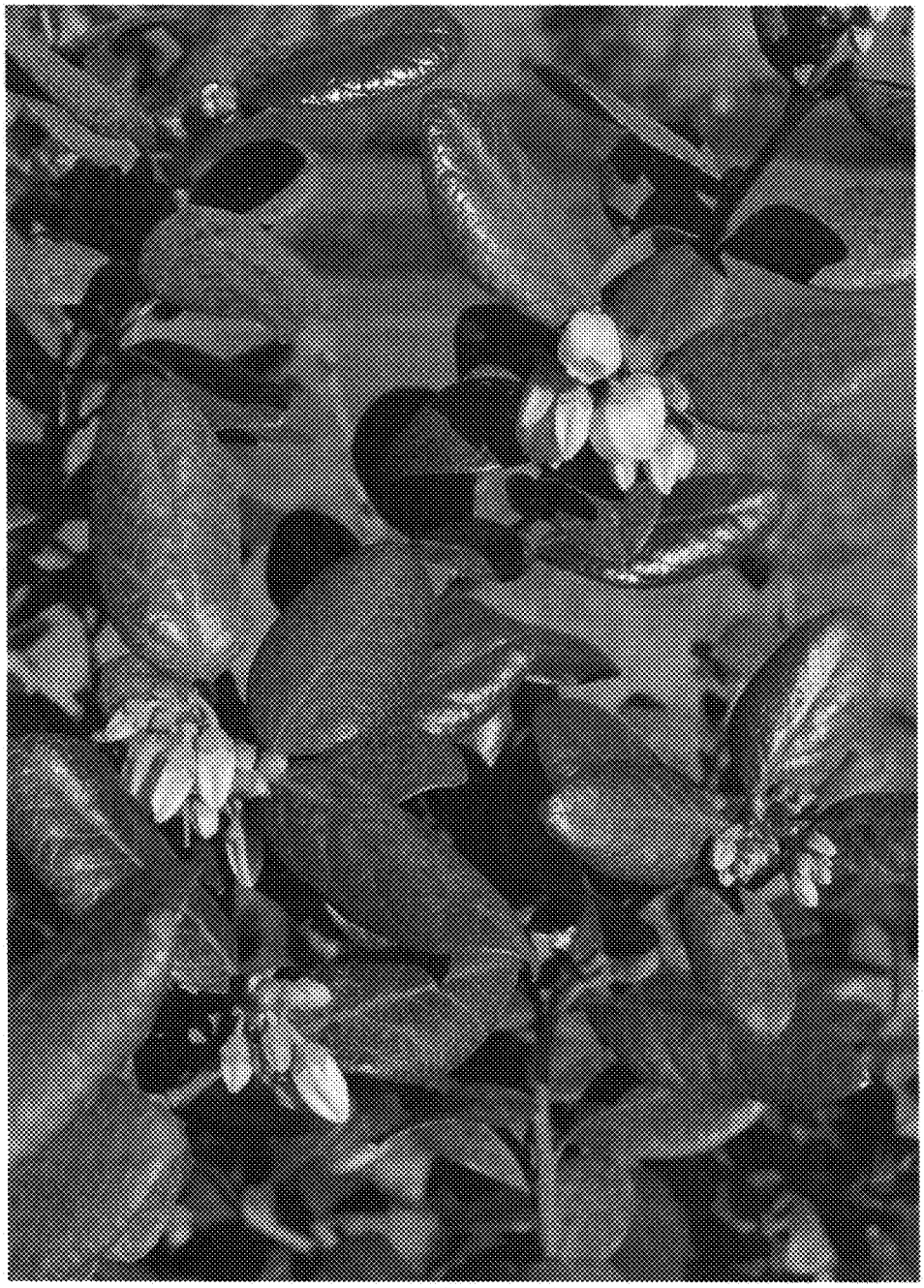
FIG. 1—Shows several clusters of opening 'FL07-399' flowers during the early stages of flowering in January in Arcadia, Fla.
Figure 2:
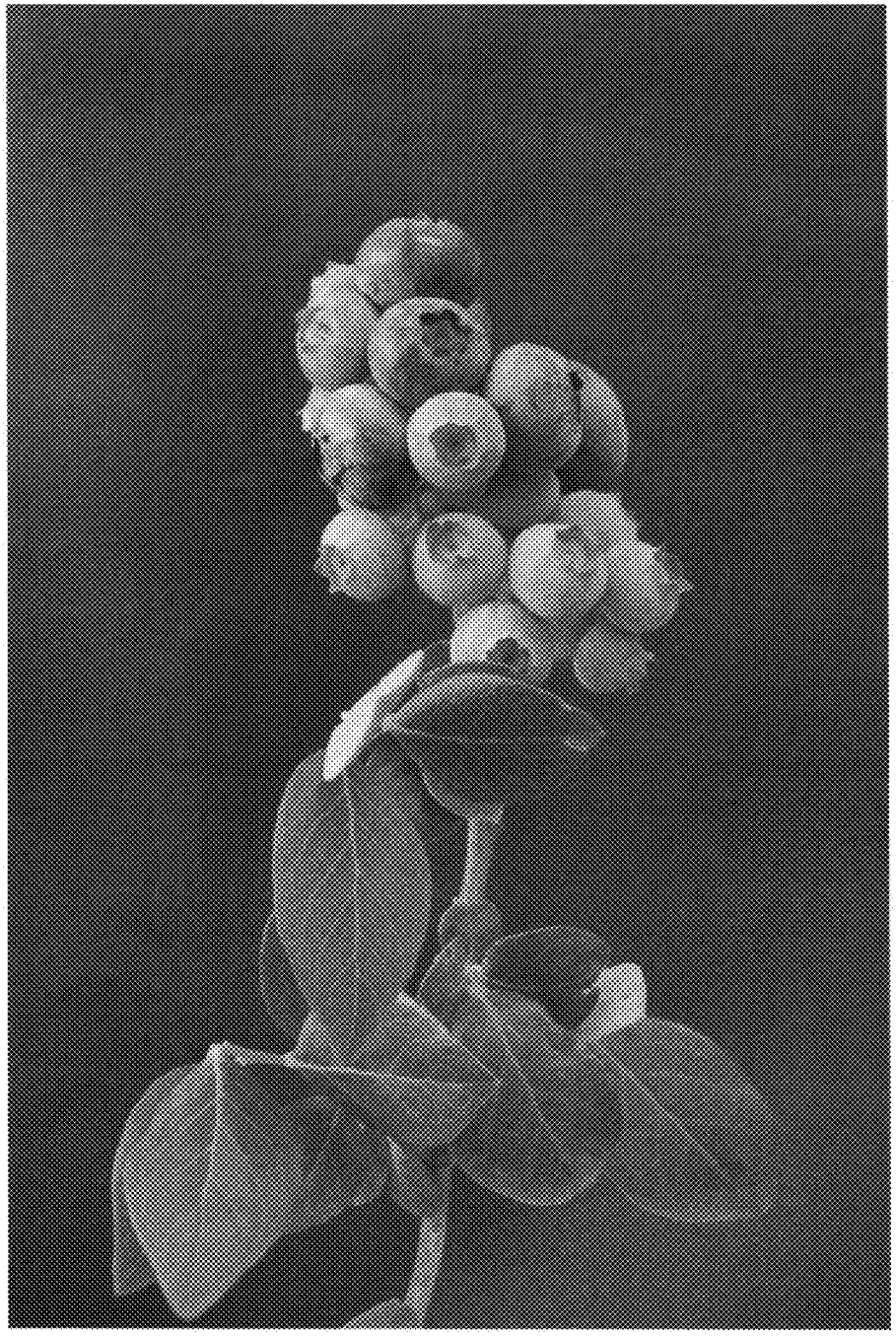
FIG. 2—Shows a cluster of 'FL07-399' berries during the fruit ripening season.
Figure 3:
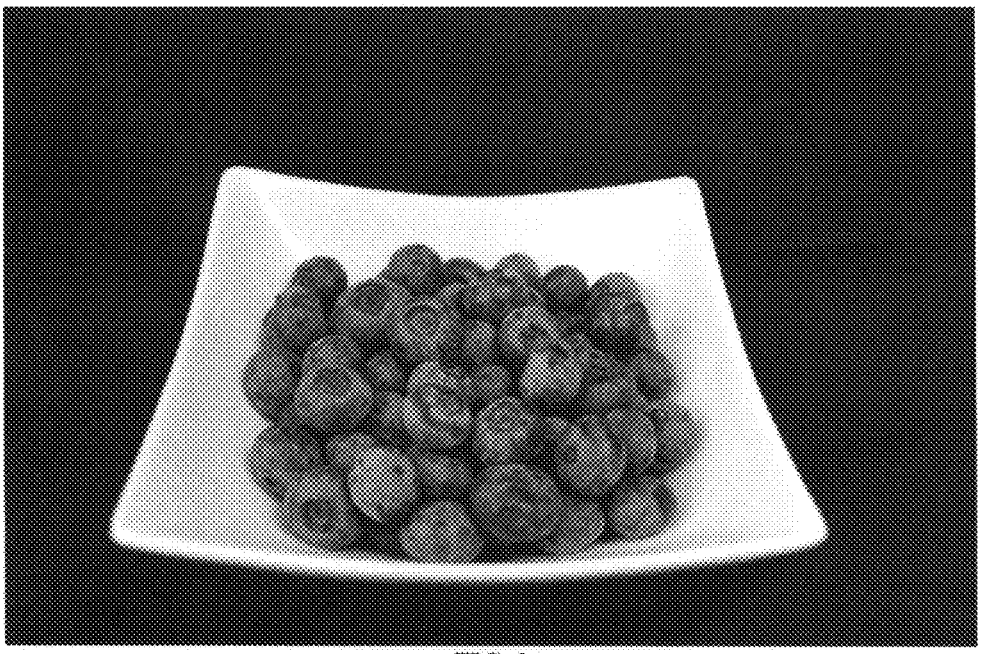
FIG. 3—Shows a close-up of harvested 'FL07-399' berries.
Figure 4:
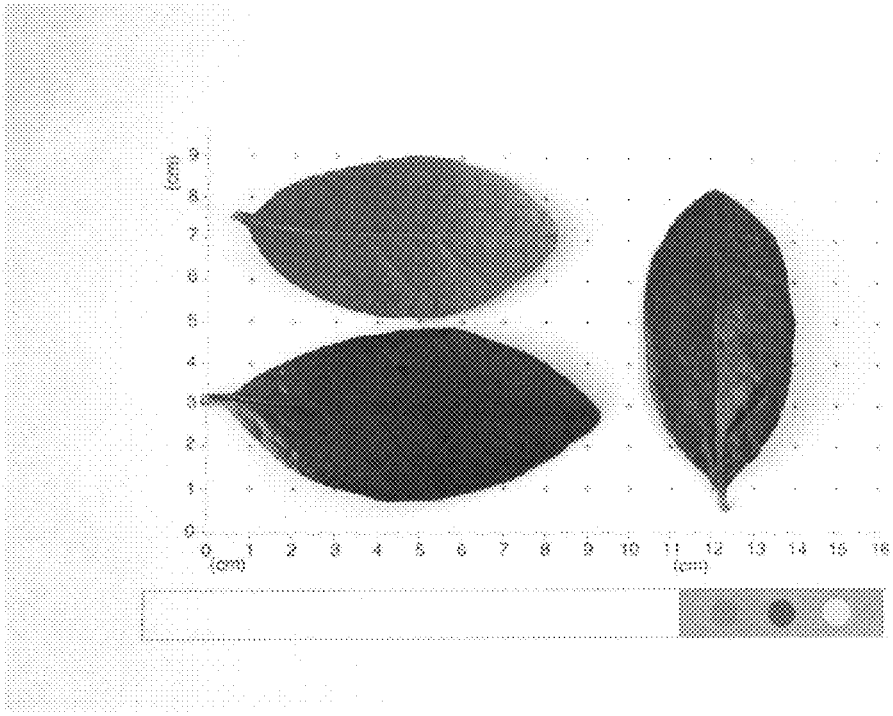
FIG. 4—Shows a close-up of mature 'FL07-399' leaves with a scale bar.
Figure 5:
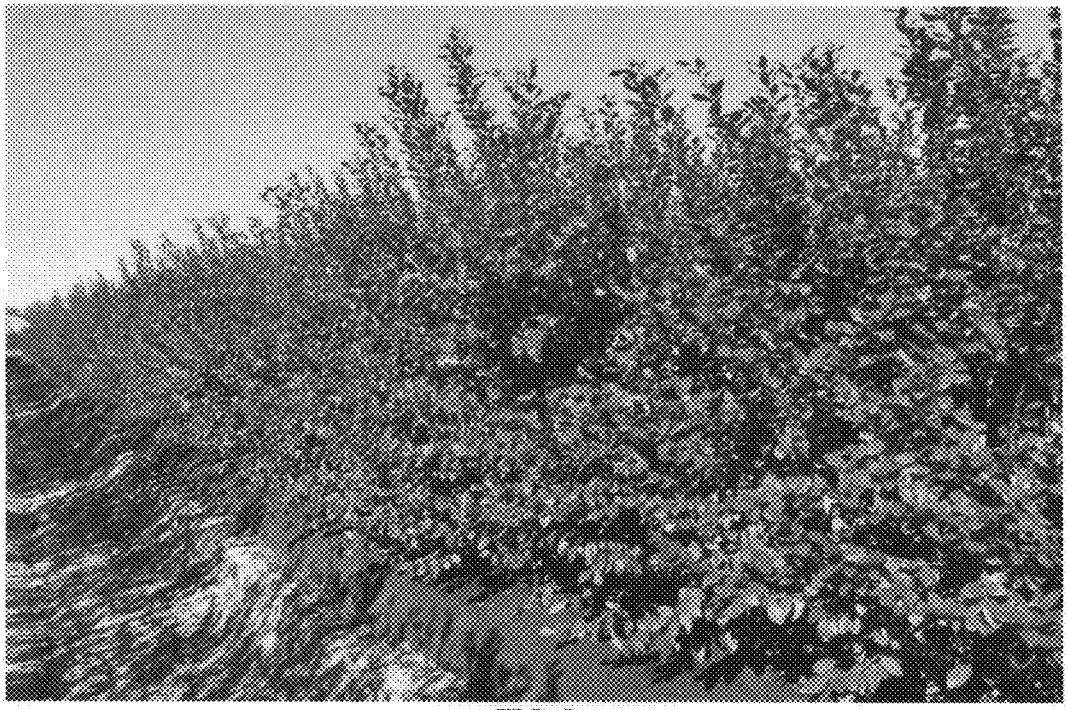
FIG. 5—Shows a three-year-old 'FL07-399' plant in December with the vigorous, upright-spreading plant architecture visible.
Figure 6:
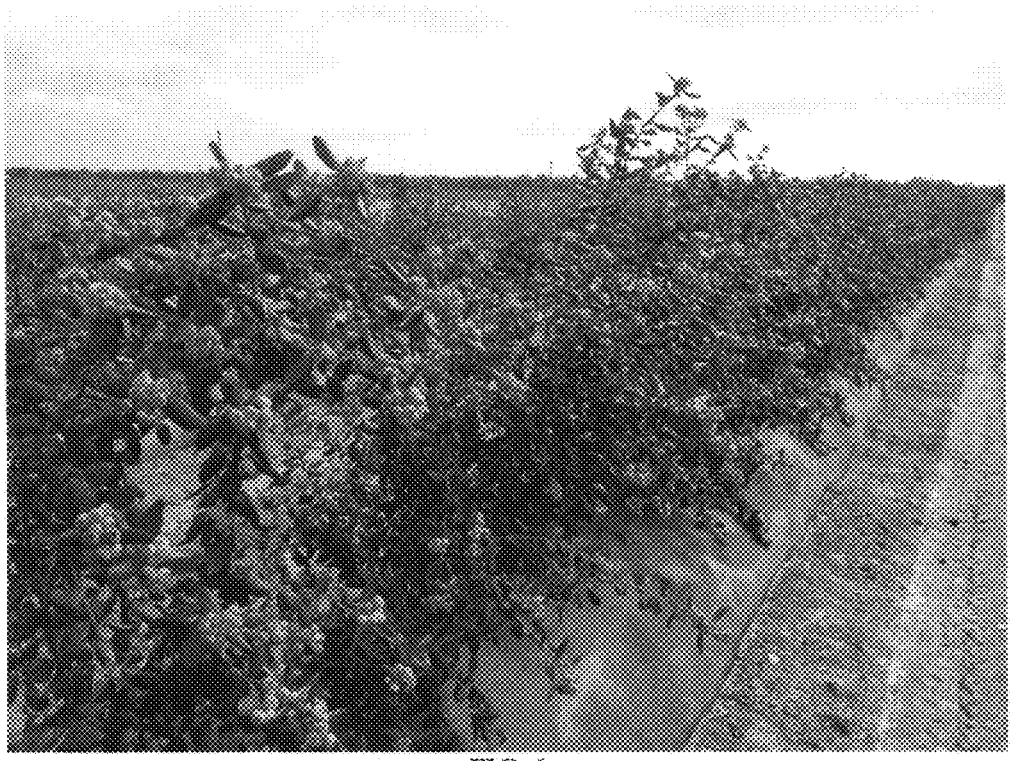
FIG. 6—Shows several two-year-old 'FL07-399' plants in early March grown in an evergreen production system near Arcadia, Fla.

The following detailed description sets forth the distinctive characteristics of 'FL07-399'. The data that define these characteristics were collected from asexual reproductions carried out in Florida. The plant history was taken on a plot of 50 four-year-old plants growing in a commercial field near Waldo, Fla. Certain characteristics may vary with plant age. 'FL07-399' has not been observed under all possible environmental conditions, and the measurements given may vary when grown in different environments. Where means are given, the sample size was 20. Color descriptions are based on The Royal Horticultural Society (R.H.S.) Colour Chart by The Royal Horticultural Society, London, Fifth Edition, 2007. When the R.H.S. color designations differ from the accompanying photographs, the R.H.S. color designations are accurate.

PHENOTYPIC DESCRIPTION OF *VACCINIUM CORYMBOSUM* L. ('FL07-399')

Plant:

*Plant vigor*.—High. Vigor is more than 'Emerald' (U.S. Plant Pat. No. 12,165).

*Growth habit*.—Upright-spreading.

*Flower bud density (number) along flowering twigs in January*.—Medium.

*Twigginess*.—High.

*Tendency toward evergreenness*.—High.

*Productivity*.—In northeast Florida, 'FL07-399' produces 2 to 3 kg per season from plants 3 years or older. In South Central Florida, 'FL07-399' produces over 5 kg per season from plants 3 years or older.

*Chilling requirement*.—When evaluated in trial sites receiving an average less than 300 hours below 7° C., 'FL07-399' has performed well.

*Cold hardiness*.—'FL07-399' has not been grown in temperate climates with extremely cold winter temperatures. Plants have survived winter freezes of −6° C. with minimal damage.

*Ease of propagation*.—'FL07-399' has only been propagated from softwood stem cuttings, where the rooting percentage has greater than 80% and is comparable to other varieties.

Trunk and branches:

*Suckering tendency*.—Low. Three-year-old plants typically have 5 to 7 major canes arising from a crown 30 cm in diameter.

*Surface texture (of strong, 6-month-old shoots observed in January)*.—Smooth.

*Surface texture (of 3-year-old and older wood)*.—Rough.

*Color of new twigs observed in the field*.—Yellow-green 144A.

*Color of 3-year-old, rough-textured canes*.—Greyed-brown 199A.

*Internode length (strong, upright shoots measured in January)*.—Mean of 15.0 mm.

Leaves:

*Length (including petiole, from tip of petiole to end of blade)*.—Mean of 8.5 cm.

*Width (at widest point)*.—Mean of 3.9 cm.

*Shape*.—Elliptic, with a rounded base and acute tip.

*Margin*.—Entire.

*Color*.—Upper surface: Green N137A. Lower surface: Greyed-green 191A.

*Pubescence*.—Upper surface of leaves: Absent. Lower surface of leaves: Absent. Margins: Absent.

*Relative time of leafing versus flowering*.—When not treated with hydrogen cyanamide in mid-winter, leafing occurs after flowering.

Flowers:

*Arrangement*.—Flowers are arranged alternately along a short, leafless, deciduous branch.

*Fragrance*.—Very slight floral fragrance.

*Shape*.—Urceolate, more rounded than cylindrical.

*Flowering period*.—Mean date of 50% open flowers in Citra, Fla. is February 12; averages 9 days later than 'Emerald' (U.S. Plant Pat. No. 12,165).

*Cluster (tight, medium, loose)*.—Loose.

*Number of flowers per cluster*.—Mean of 6.3.

*Pedicel*.—Length at time of anthesis: Mean of 9.1 mm. Color at time of anthesis: Yellow-green 150B with Greyed-orange 174B on the sun-exposed side.

*Peduncle*.—Length at time of anthesis: Highly variable, mean of 11.8 mm. Color at time of anthesis: Green-yellow 1C with Greyed-red 181B on sun-exposed side.

*Calyx*.—Surface texture: Smooth. Diameter: Mean of 6.8 mm. Color: Yellow-green 145B to Yellow-green 147B on tips of calyx lobes.

*Corolla*.—Diameter: Mean of 9.2 mm. Length (from pedicel attachment point to corolla tip excluding the pedicel): Mean of 11.5 mm. Aperture diameter: Mean of 4.8 mm. Texture: Smooth. Color: Green-white 157C.

Reproductive organs:

*Style*.—Length (top of ovary to stigma tip): Mean of 10.9 mm. Color: Yellow-green 145B. Location of tip of stigma relative to lip of the corolla — Stigma tip is approximately even with the corolla lip.

*Anthers*.—Color: Greyed-orange 167A. Pollen — Abundance of shed: High. Pollen germination: Typically greater than 90%. Color: Yellow-white 158C.

*Self-fruitfulness*.—Low to medium. Planting in field configurations that promote cross fertilization with other southern highbush varieties is recommended for all southern highbush blueberry plants grown in Florida.

Fruit:

*Mean date of 50% harvest in Citra, Fla*.—April 25.

*Diameter of calyx aperture on mature berry*.—Mean of 8.5 mm.

*Size and shape of calyx lobes on mature berry*.—Very small to absent, flat to incurving. Shallow to medium calyx basin.

*Pedicel length on ripe berry*.—Mean of 6.5 mm.

*Detachment force for ripe berries* (*easy, medium, hard*).—Medium to easy.

*Number of berries per cluster*.—Mean of 5.3.

Berry:

*Cluster* (*tight, medium, loose*).—Medium.

*Weight* (*on well-pruned plants*).—Mean of 3.1 g.

*Height*.—Mean of 13.2 mm.

*Width*.—Mean of 19.1 mm.

*Shape*.—Oblate.

*Surface color of mature berries ripe on the plant*.—Violet-blue 98D.

*Surface color of ripe berry after polishing*.—Black 202A.

*Immature berry color, with bloom*.—Greyed-green 193B.

*Immature berry color, without bloom*.—Yellow-green 146D.

*Surface wax*.—High. The surface wax on 'FL07-399' has only medium persistence.

*Pedicel scar*.—Small and dry. Mean of 3.2 mm.

*Firmness*.—Firm.

*Flavor*.—Sweet.

*Texture*.—Smooth, meaty texture, medium seeds, and no stone cells present.

Seeds:

*Color of dried seeds*.—Greyed-orange 164A.

*Weight of well-developed dried seed*.—Mean of 0.7 mg.

*Length of well-developed dried seed*.—Mean of 2.4 mm.

*Width of well-developed dried seed*.—Mean of 1.2 mm.

Use: 'FL07-399' produces southern highbush blueberries suitable for both the fresh and processed fruit markets. 'F107-399' has performed best in trials when grown under an evergreen management system.

Resistance to diseases, insects, and mites: 'FL07-399' has grown vigorously and shows excellent bush survival in the field. It appears to be resistance to stem blight (*Botryosphaeria* spp.) and root rot (*Phytophthora cinnamoni*), with very few young plants dying soon after planting. The reaction of 'FL07-399' to the fungal species that cause summer leaf spots is typical of other southern highbush varieties, and fungicide applications may be needed after harvest to reduce foliar diseases and retain leaves as an evergreen plant.

What is claimed is:

1. A new and distinct southern highbush blueberry plant named 'FL07-399', as illustrated and described herein.

* * * * *